United States Patent
Cheng et al.

[11] Patent Number: 6,043,227
[45] Date of Patent: Mar. 28, 2000

[54] C11 CARBAMATES OF MACROLIDE ANTIBACTERIALS

[75] Inventors: Hengmiao Cheng, East Lyme; Michael Letavic, Mystic; Carl B. Ziegler, Jr., East Lyme; Jason K. Dutra, Groton; Peter Bertinato, Old Lyme; Brian S. Bronk, Gales Ferry, all of Conn.

[73] Assignee: Pfizer Inc., New York, N.Y.

[21] Appl. No.: 09/320,352

[22] Filed: May 26, 1999

Related U.S. Application Data

[60] Provisional application No. 60/097,075, Aug. 19, 1998, and provisional application No. 60/104,785, Oct. 19, 1998.

[51] Int. Cl.$^7$ .............................. A61K 31/70; C07H 17/08
[52] U.S. Cl. .............................. 514/29; 536/7.4; 536/18.5
[58] Field of Search ........................... 536/7.2, 7.4, 18.5; 514/29

[56] References Cited

U.S. PATENT DOCUMENTS

| | | | |
|---|---|---|---|
| 4,921,839 | 5/1990 | Brain et al. | 514/29 |
| 5,434,140 | 7/1995 | Kobrehel et al. | 514/30 |

*Primary Examiner*—Elli Peselev
*Attorney, Agent, or Firm*—Peter C. Richardson; Paul H. Ginsburg; Jolene W. Appleman

[57] ABSTRACT

This invention relates to compounds of the formula

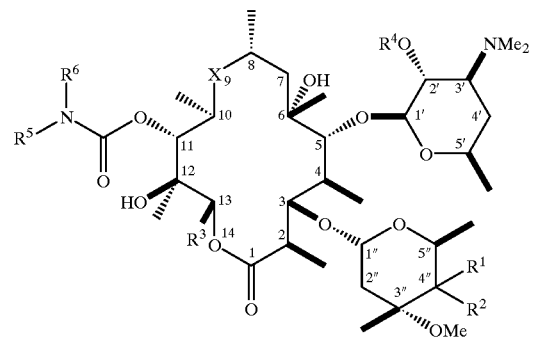

and to pharmaceutically acceptable salts thereof. The compounds of formula 1 are potent antibacterial agents that may be used to treat various bacterial infections and disorders related to such infections. The invention also relates to pharmaceutical compositions containing the compounds of formula 1 and to methods of treating bacterial infections by administering the compounds of formula 1. The invention also relates to methods of preparing the compounds of formula 1 and to intermediates useful in such preparation.

10 Claims, No Drawings

C11 CARBAMATES OF MACROLIDE ANTIBACTERIALS

This application claims benefit of Provisional Application No. 60/097,075 filed Aug. 19, 1998 and Provisional Application No. 60/104,785 filed Oct. 19, 1998.

BACKGROUND OF THE INVENTION

This invention relates to novel C11 carbamate azalide derivatives that are useful as antibacterial and antiprotozoa agents in mammals, including man, as well as in fish and birds. This invention also relates to pharmaceutical compositions containing the novel compounds and to methods of treating bacterial and protozoa infections in mammals, fish and birds by administering the novel compounds to mammals, fish and birds requiring such treatment.

Macrolide antibiotics are known to be useful in the treatment of a broad sprectrum of bacterial infections in mammals, fish and birds. Such antibiotics include various derivatives of erythromycin A such as azithromycin which is commercially available and is referred to in U.S. Pat. Nos. 4,474,768 and 4,517,359, both of which are incorporated herein by reference in their entirety. Additional macrolides are referred to in United States provisional patent application Ser. No. 60/049349, filed Jun. 11, 1997 (Yong-Jin Wu); in United States provisional patent application Ser. No. 60/046150, filed May 9, 1997 (Yong-Jin Wu); in United States provisional patent application Ser. No. 60/063676, filed Oct. 29, 1997 (Yong-Jin Wu); United States provisional patent application Ser. No. 60/063161, filed Oct. 29, 1997 (Yong-Jin Wu); United States provisional patent application Ser. No. 60/054866, filed Aug. 6, 1997 (Wei-Guo Su, Bingwei V. Yang, Robert G. Linde, Katherine E. Brighty, Hiroko Masamune, Yong-Jin Wu, Takushi Kaneko and Paul R. McGuirk); United States provisional patent application Ser. No. 60/049348, filed Jun. 11, 1997 (Brian S. Bronk, Michael A. Letavic, Takushi Kaneko and Bingwei V. Yang); International Application No. PCT/GB97/01810 filed Jul. 4, 1997 (Peter Francis Leadlay, James Staunton, Jesus Cortes and Michael Stephen Pacey); International Application No. PCT/GB97101819, filed Jul. 4, 1997 (Peter Francis Leadlay, James Staunton, and Jesus Cortes); United States); United States provisional patent application Ser. No. 60/070343, entitled "Novel Macrolides", filed Jan. 2, 1998 (John P. Dirlam); and United States provisional patent application entitled "Novel Erythromycin Derivatives", filed Jan. 2, 1998 (Yong-Jin Wu); all of which are incorporated herein by reference in their entirety. Like azithromycin and other macrolide antibiotics, the novel macrolide compounds of the present invention possess potent activity against various bacterial infections as described below.

SUMMARY OF THE INVENTION

The present invention relates to compounds of the formula

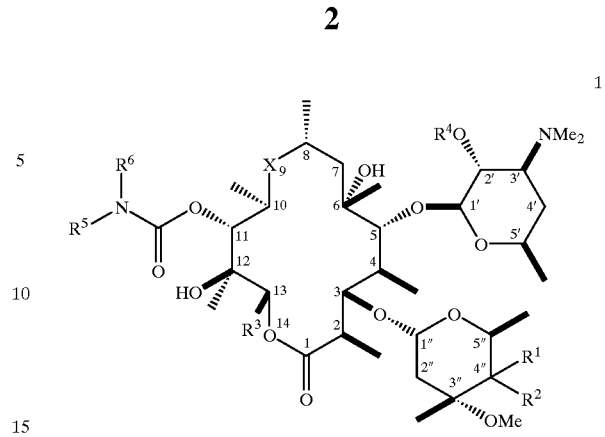

and to pharmaceutically acceptable salts thereof, wherein:

X is —CH$_2$NR$^7$—, or —NR$^7$CH$_2$— wherein the first dash of each of the foregoing X groups is attached to C-10 carbon of the compound of formula 1 and the last dash of each group is attached to the C-8 carbon of the compound of formula 1;

R$^1$ is hydroxy;

R$^2$ is H, C$_{1-C10}$ alkyl, C$_2$–C$_{10}$-alkenyl. C$_2$–C$_{10}$ alkynyl, cyano, —CH$_2$S(O)$_n$R$^8$ wherein n is an integer ranging from 0 to 2, —CH$_2$OR$^8$, —CH$_2$NR$^8$R$^9$, —(CH$_2$)$_m$(C$_6$–C$_{10}$ aryl), or —(CH$_2$)$_m$(5–10 membered heteroaryl), wherein m is an integer ranging from 0 to 4, and wherein the alkyl, alkenyl, alkynyl, aryl and heteroaryl moieties of the foregoing R$^2$ groups are optionally substituted by 1 to 3 substituents independently selected from halo, cyano, nitro, trifluoromethyl, azido, —C(O)RB, —OC(O)R$^8$, —NR$^8$C(O)R$^9$, —C(O)NR$^5$R$^9$, —NR$^8$R$^9$, hydroxy, C$_{1-C6}$ alkyl, C$_1$–C$_6$ alkoxy, C$_6$–C$_{10}$ aryl, and 5–10 membered heteroaryl;

R$^3$ is an alpha-branched C$_2$–C$_8$ alkyl, alkenyl, alkynyl, alkoxyalkyl or alkylthioalkyl group any of which may optionally be substituted by one or more hydroxyl groups; a C$_5$–C$_8$ cycloalkylalkyl group wherein the alkyl group is an alpha-branched C$_2$–C$_5$ alkyl group; a C$_3$–C$_8$ cycloalkyl or C$_5$–C$_8$ cycloalkenyl group, either of which may optionally be substituted by methyl or one or more hydroxyl or one or more C$_1$–C$_4$ alkyl groups or halo atoms; or a 3 to 6 membered oxygen or sulphur containing heterocyclic ring which may be saturated, or fully or partially unsaturated and which may optionally be substituted by one or more C$_1$–C$_4$ alkyl groups or halo atoms; specific preferred examples of R$^3$ are ethyl, isopropyl, cyclopropyl, secbutyl, cyclobutyl, cyclopentyl, methylthioethyl, furyl;

3Or R$^3$ is phenyl which may be optionally substituted with at least one substituent selected from C$_1$–C$_4$ alkyl, C$_1$–C$_4$ alkoxy and C$_1$–C$_4$ alkylthio groups, halogen atoms, hydroxyl groups, trifluoromethyl, and cyano;

R$^4$ is H or a hydroxy protecting group;

each R$^5$ and R$^6$ is independently H, C$_1$–C$_{10}$ alkyl, C$_2$–C$_{10}$ alkenyl, C$_2$–C$_{10}$ alkynyl, —(CH$_2$)$_m$C$_6$–C$_{10}$ aryl, —(CH$_2$)$_m$(5–10 membered heteroaryl), wherein m is an integer ranging from 0 to 4, and wherein the alkyl, alkenyl, aryl, heteroaryl and alkynyl moieties of the foregoing R$^5$ and R$^6$ groups are optionally substituted by 1 to 3 substituents independently selected from halo, cyano, nitro, trifluoromethyl, azido, —C(O)R$^8$, —OC(O)R$^8$, —NR$^8$C(O)R$^9$, —C(O)NR$^8$R$^9$, —NR$^8$R$^9$, hydroxy, C$_1$–C$_6$ alkyl, C$_1$–C$_6$ alkoxy, C$_6$–C$_{10}$ aryl, and 5–10 membered heteroaryl; or R$^5$ and R$^6$ may be taken together to form a 4–7 membered saturated ring or a 5–10 membered heteroaryl ring, wherein said saturated and heteroaryl rings optionally include 1 or 2 heteroatoms selected from O, S, and N, in addition to the nitrogen to which $R^5$ and $R^6$ are attached, said saturated ring optionally includes 1 or 2 carbon-carbon double or triple bonds, and said saturated and heteroaryl rings are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl and 5–10 membered heteroaryl;

$R^7$ is H, $C_1$–$C_{10}$ alkyl, $C_2$–$C_{10}$ alkenyl, $C_2$–$C_{10}$ alkynyl, —(CH$_2$)$_m$C$_6$–$C_{10}$ aryl, —(CH$_2$)$_m$(5–10 membered heteroaryl), wherein m is an integer ranging from 0 to 4, and wherein the alkyl, alkenyl, aryl, heteroaryl and alkynyl moieties of the foregoing $R^5$ and $R^6$ groups are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and 5–10 membered heteroaryl;

each $R^8$ and $R^9$ is independently H, hydroxy, $C_1$–$C_6$ alkoxy, $C_1$–$C_6$ alkyl, $C_2$–$C_6$ alkenyl, (CH$_2$)$_m$(C$_6$–$C_{10}$ aryl), (CH$_2$)$_m$(5–10 membered heteroaryl), wherein m is an integer ranging from 0 to 4, or $C_2$–$C_{10}$ alkylyl; and Me is methyl.

Prefered compounds of formula 1 include those wherein $R^1$ is hydroxy, $R^2$ is H or methyl, $R^3$ is ethyl, $R^4$ is H, $R^5$ is H, $R^6$ is $C_1$–$C_{10}$ alkyl, $C_2$–$C_{10}$ alkenyl, $C_2$–$C_2$–$C_{10}$ alkynyl, —(CH$_2$)$_m$C$_6$–$C_{10}$ aryl, —(CH$_2$)$_m$(5–10 membered heteroaryl), wherein m is an integer ranging from 0 to 4, and wherein the alkyl, alkenyl, alkynyl, aryl and heteroaryl moieties of the foregoing $R^6$ group are optionally substituted by 1 to 3 substituents independently selected from halo, cyano, nitro, trifluoromethyl, azido, hydroxy, $C_1$–$C_6$ alkyl, $C_1$–$C_6$ alkoxy, $R^7$ is H, Me, Et, propyl, butyl, cyclopropylmethyl. Specific prefered compounds having the foregoing general structure include those wherein $R^6$ is 2-pyridylmethyl, 3-pyridylmethyl, 4-pyridylmethyl, 2-pyridylethyl, 3-pyridylethyl, 4-pyridylethyl, 2-fluorobenzyl, 3-fluorobenzyl, 4-fluorobenzyl, 2,3-dimethoxybenzyl, 2,4-dimethoxybenzyl, 2,5-dimethoxybenzyl, 2,6-dimethoxybenzyl, 3,4-dimethoxybenzyl, 3,5-dimethoxybenzyl, 3,6-dimethoxybenzyl, 3,4-dimethoxyphenylethyl, allyl, propyl, isopropyl.

The invention also relates to a pharmaceutical composition for the treatment of a bacterial infection or a protozoa infection in a mammal, fish, or bird which comprises a therapeutically effective amount of a compound of formula 1, or a pharmaceutically acceptable salt thereof, and a pharmaceutically acceptable carrier.

The invention also relates to a method of treating cancer, in particular non-small cell lung cancer, in a mammal, which comprises adminstering to said mammal a therapeutically effective amount of a compound of formula 1 or a pharmaceutically acceptable salt or solvate thereof.

The invention also relates to a method of treating a bacterial infection or a protozoa infection in a mammal, fish, or bird which comprises administering to said mammal, fish or bird a therapeutically effective amount of a compound of formula 1 or a pharmaceutically acceptable salt thereof.

The term "treatment", as used herein, unless otherwise indicated, includes the treatment or prevention of a bacterial infection or protozoa infection as provided in the method of the present invention.

As used herein, unless otherwise indicated, the terms "bacterial infection(s)" and "protozoa infection(s)" include bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections, and disorders related to such infections, include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus,* or Peptostreptococcus spp.; pharynigitis, rheumatic fever, and glomerulonephritis related to infection by *Streptococcus pyogenes,* Groups C and G streptococci, *Clostridium diptheriae,* or *Actinobacillus haemolyticum;* respiratory tract infections related to infection by *Mycoplasma pneumoniae, Legionella pneumophila, Streptococcus pneumoniae, Haemophilus influenzae,* or *Chlamydia pneumoniae;* uncomplicated skin and soft tissue infections, abscesses and osteomyelitis, and puerperal fever related to infection by *Staphylococcus aureus,* coagulase-positive staphylococci (i.e., *S. epidermidis, S. hemolyticus,* etc.), *Streptococcus pyogenes, Streptococcus agalactiae,* Streptococcal groups C–F (minute-colony streptococci), viridans streptococci, *Corynebacterium minutissimum,* Clostridium spp., or *Bartonella henselae;* uncomplicated acute urinary tract infections related to infection by *Staphylococcus saprophyticus* or Enterococcus spp.; urethritis and cervicitis; and sexually transmitted diseases related to infection by *Chlamydia trachomatis, Haemophilus ducreyi, Treponema pallidum, Ureaplasma urealyticum,* or *Neiserria gonorrheae;* toxin diseases related to infection by *S. aureus* (food poisoning and Toxic shock syndrome), or Groups A, B, and C streptococci; ulcers related to infection by *Helicobacter pylori;* systemic febrile syndromes related to infection by *Borrelia recurrentis;* Lyme disease related to infection by *Borrelia burgdorferi,* conjunctivitis, keratitis, and dacrocystitis related to infection by *Chlamydia trachomatis, Neisseria gonorrhoeae, S. aureus, S. pneumoniae, S. pyogenes, H. influenzae,* or Listeria spp.; disseminated *Mycobacterium avium* complex (MAC) disease related to infection by *Mycobacterium avium,* or *Mycobacterium intracellulare;* gastroenteritis related to infection by *Campylobacter jejuni;* intestinal protozoa related to infection by Cryptosporidium spp.; odontogenic infection related to infection by viridans streptococci; persistent cough related to infection by *Bordetella pertussis;* gas gangrene related to infection by *Clostridium perfringens* or Bacteroides spp.; and atherosclerosis related to infection by *Helicobacter pylori* or *Chlamydia pneumoniae.* Bacterial infections and protozoa infections and disorders related to such infections that may be treated or prevented in animals include the following: bovine respiratory disease related to infection by *P. haem., P. multocida, H. somnus, Mycoplasma bovis,* or Bordetella spp.; cow enteric disease related to infection by *E. coli* or protozoa (i.e., coccidia, cryptosporidia, etc.); dairy cow mastitis related to infection by *Staph. aureus, Strep. uberis, Strep. agalactiae, Strep. dysgalactiae,* Klebsiella spp., Corynebacterium, or Enterococcus spp.; swine respiratory disease related to infection by *A. pleuro., P. multocida,* or Mycoplasma spp.; swine enteric disease related to infection by *E. coli, Lawsonia intracellularis,* Salmonella, or *Serpulina hyodyisinteriae;* cow footrot related to infection by Fusobacterium spp.; cow metritis related to infection by *E. coli;* cow hairy warts related to infection by *Fusobacterium necrophorum* or *Bacteroides nodosus;* cow pink-eye related to infection by

*Moraxella bovis;* cow premature abortion related to infection by protozoa (i.e. neosporium); urinary tract infection in dogs and cats related to infection by *E. coli;* skin and soft tissue infections in dogs and cats related to infection by *Staph. epidermidis, Staph. intermedius, coagulase neg. Staph.* or *P. multocida;* and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoa infections and disorders related to such infections that may be treated or prevented in accord with the method of the present invention are referred to in J. P. Sanford et al., "The Sanford Guide To Antimicrobial Therapy," 26th Edition, (Antimicrobial Therapy, Inc., 1996).

The present invention also relates to a method of preparing the above compound of formula 1, or a pharmaceutically acceptable salt thereof, wherein $R^5$ is H, $R^6$ is $C_1$–$C_{10}$ alkyl, $C_2$–$C_{10}$ alkenyl, $C_2$–$C_{10}$ alkynyl, —$(CH_2)_m C_6$–$C_{10}$ aryl, —$(CH_2)_m$(5–10 membered hetroaryl), wherein m is an integer ranging from 0 to 4, which comprises treating a compound of the formula 2

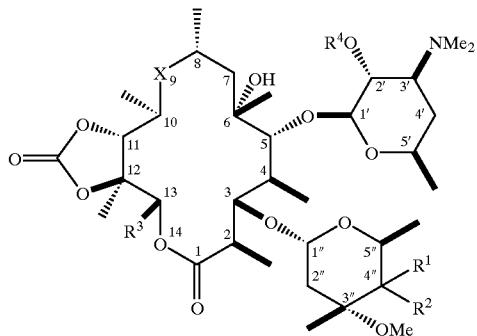

wherein X, $R^1$, $R^2$, $R^3$ and $R^4$ are as defined above, with a compound of the formula $HNR^5R^6$, wherein $R^5$ and $R^6$ are as defined above.

In a further aspect of the above process of preparing the compound of formula 1, or a pharmaceutically acceptable salt thereof, the above compound of formula 2 is prepared by treating a compound of the formula 3

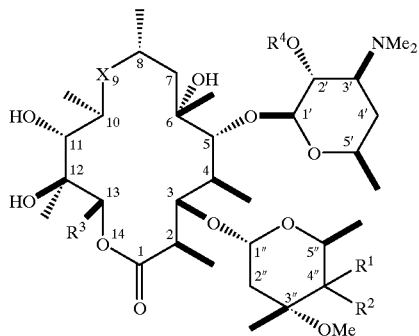

wherein X, $R^1$, $R^2$, $R^3$ and $R^4$ are as defined above, with a suitable reagent such as ethylene carbonate, in the presence of a base such as as potassium carbonate, in a liquid such as ethyl acetate at 75° C.

The present invention also relates to the above compounds of formula 2, as indicated above, useful in the preparation of the above compounds of formula 1 and pharmaceutically acceptable salts thereof.

The term "hydroxy protecting group", as used herein, unless otherwise indicated, includes acetyl, benzyloxycarbonyl, and various hydroxy protecting groups familiar to those skilled in the art including the groups referred to in T. W. Greene, P. G. M. Wuts, "Protective Groups In Organic Synthesis," (J. Wiley & Sons, 1991).

The term "halo", as used herein, unless otherwise indicated, includes fluoro, chloro, bromo or iodo.

The term "alkyl", as used herein, unless otherwise indicated, includes saturated monovalent hydrocarbon radicals having straight, cyclic or branched moieties, or mixtures thereof. It is to be understood that where cyclic moieties are intended, at least three carbons in said alkyl must be present. Such cyclic moieties include cyclopropyl, cyclobutyl and cyclopentyl.

The term "alkoxy", as used herein, unless otherwise indicated, includes —O-alkyl groups wherein alkyl is as defined above.

The term "aryl", as used herein, unless otherwise indicated, includes an organic radical derived from an aromatic hydrocarbon by removal of one hydrogen, such as phenyl or naphthyl.

The term "5–10 membered heteroaryl", as used herein, unless otherwise indicated, includes aromatic heterocyclic groups containing one or more heteroatoms each selected from O, S and N, wherein each heterocyclic group has from 5 to 10 atoms in its ring system. Examples of suitable 5–10 membered heteroaryl groups include pyridinyl, imidazolyl, pyrimidinyl, pyrazolyl, (1,2,3,)- and (1,2,4)-triazolyl, pyrazinyl, tetrazolyl, furyl, thienyl, isoxazolyl, oxazolyl, pyrrolyl and thiazolyl.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include an amino moiety may form pharmaceutically acceptable salts with various amino acids, in addition to the acids mentioned above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

Certain compounds of the present invention may have asymmetric centers and therefore exist in different enantiomeric and diastereomic forms. This invention relates to the use of all optical isomers and stereoisomers of the compounds of the present invention, and mixtures thereof, and to all pharmaceutical compositions and methods of treatment that may employ or contain them.

The present invention includes the compounds of the present invention, and the pharmaceutically acceptable salts thereof, wherein one or more hydrogen, carbon or other atoms are replaced by isotopes thereof. Such compounds may be useful as research and diagnostic tools in metabolism pharmacokinetic studies and in binding assays.

DETAILED DESCRIPTION OF THE INVENTION

The compounds of of the present invention may be prepared according to Scheme 1 below and the description that follows. In the following Schemes, unless otherwise indicated, substituents X, $R^1$, $R^2$, $R^3$, $R^4$, $R^5$, $R^6$, $R^7$, $R^8$, and $R^9$ are as defined above.

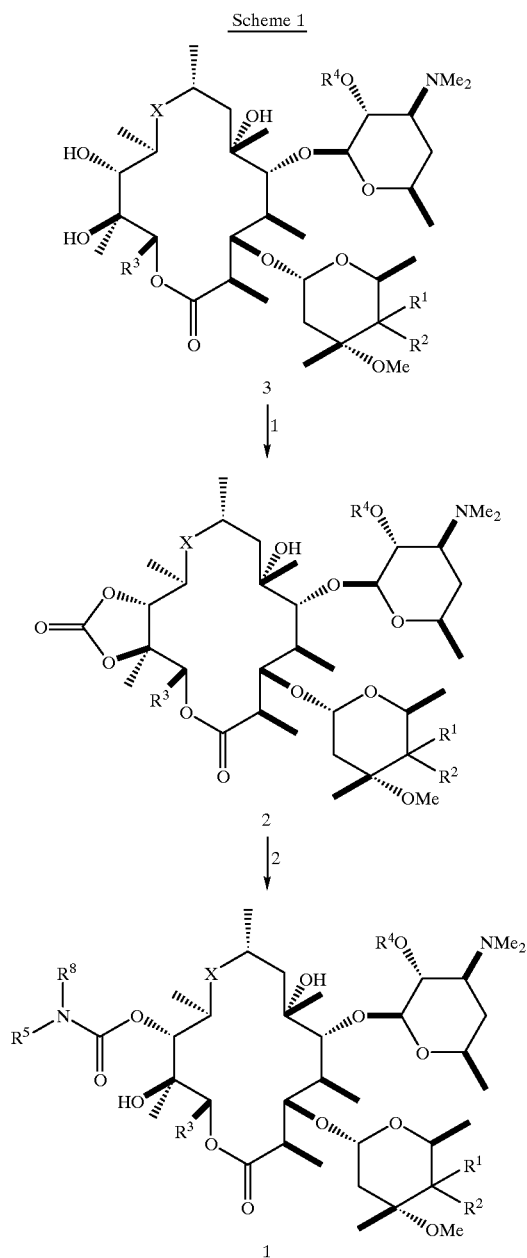

Scheme 1

This invention uses the following macrolide templates as starting materials: desmethyl-azithromycin, desmethyl-isoazithromycin as well as their analogs. Azithromycin can be prepared according to methods described in U.S. Pat. Nos. 4,474,768 and 4,517,359, referred to above. Isoazithromycin can be prepared according to methods described in European Patent Publication 0508699.

The foregoing starting materials require proper functional group protection before various modifications can take place, and deprotection after desired modifications are complete. The most commonly used protecting groups for amino moieties in the macrolide compounds of this invention are benzyloxycarbonyl (Cbz) and t-butyloxycarbonyl (Boc) groups. Hydroxyl groups are generally protected as acetates or Cbz carbonates. The relative reactivity of various hydroxyl groups in the macrolide molecules of the general type claimed in this invention has been well established. Such differences in reactivity permit selective modification of different parts of the compounds of this invention.

In the above Schemes, the C-2' hydroxy group ($R^4$ is H) is selectively protected by treating the macrolide compound with one equivalent of acetic anhydride in dichloromethane in the absence of external base to provide the corresponding compound wherein $R^4$ is acetyl. The acetyl protecting group may be removed by treating the compound of formula 3 with methanol at 23–65° C. for 10–48 hours. The C-2' hydroxy may also be protected with other protecting groups familiar to those skilled in the art, such as the Cbz group. Where X is —$CH_2NH$—, the C-9 amino group may also require protection before further synthetic modifications are performed. Suitable protecting groups for the amino moiety are Cbz and Boc groups. To protect the C-9 amino group, the macrolide may be treated with t-butyl dicarbonate in anhydrous tetrahydrofuran (THF) or benzyloxycarbonyl N-hydroxysuccinimide ester or benzylchloroformate to protect the amino group as its t-butyl or benzyl carbamate. Both the C-9 amino and C-2' hydroxy may be selectively protected with the Cbz group in one step by treating the compound of formula 2 with benzylchloroformate in THF and water. The Boc group may be removed by acid treatment and the Cbz group may be removed by conventional catalytic hydrogenation. In the following description, it is assumed that, where X is —$CH_2NH$—, the C-9 amino moiety as well as the C-2' hydroxy group are protected and deprotected as would be deemed appropriate by those skilled in the art.

In Scheme 1, the compound of formula 3 may be prepared according to methods familiar to those skilled in the art. In step 1 of Scheme 1, the compound of formula 3 is treated with a suitable carbonate forming reagent such as ethylene carbonate, in the presence of a base such as potassium carbonate, in a solvent such as EtOAc, at temperature ranging from 23 to 75° C., to provide the compound of formula 2. In step 2 of Scheme 1, the compound of formula 2 is treated with $HNR^5R^6$ wherein $R^5$ and $R^6$ are as defined as above, a catalytic amount of pyridine hydrochloride can be added, N—Me-imidazole can be used as both a solvent and catalyst to accelerate the reaction when lipophilic aromatic amines such as fluorobenzyl amine and methoxybenzylamine were used. The resulting solution is stirred at a temperature ranging from 23° C. to 75° C. for two to five days to provide the compound of formula 1.

The compounds of the present invention may have asymmetric carbon atoms and therefore exist in different enantiomeric and diastereomeric forms. Diastereomeric mixtures can be separated into their individual diastereomers on the basis of their physical chemical differences by methods known to those skilled in the art, for example, by chromatography or fractional crystallization. Enantiomers may be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. Such separations may also be accomplished through use of standard chiral HPLC. The use of all such isomers, including diastereomer mixtures and pure enantiomers, are considered to be part of the present invention.

The compounds of the present invention that are basic in nature are capable of forming a wide variety of different salts with various inorganic and organic acids. Although such salts must be pharmaceutically acceptable for administration to mammals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired salt can also be precipitated from a solution of the free base in an organic solvent by adding to the solution an appropriate mineral or organic acid.

Those compounds of the present invention that are acidic in nature are capable of forming base salts with various cations. For compounds that are to be administered to mammals, fish or birds such salts must be pharmaceutically acceptable. Where a pharmaceutically acceptable salt is required, it may be desirable to initially isolate the compound of the present invention from the reaction mixture as a pharmaceutically unacceptable salt and then simply convert the latter to a pharmaceutically acceptable salt in a process analogous to that described above relating to the conversion of pharmaceutically unacceptable acid addition salts to pharmaceutically acceptable salts. Examples of base salts include the alkali metal or alkaline-earth metal salts and particularly the sodium, amine and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium, calcium, magnesium, various amine cations, etc. These salts can easily be prepared by treating the corresponding acidic compounds with an aqueous solution containing the desired pharmacologically acceptable bases with cations such as sodium, potassium, calcium, magnesium, various amine cations, etc., and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The activity of the compounds of the present invention in the treatment of a bacterial, parasitic or protozoal infection, or a disorder related to a bacterial, parasitic or protozoal infection, may be assessed by subjecting the claimed compounds to one or more of the following assays.

ASSAY I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562–2566 (1996). The assay is performed in microtiter trays and interpreted according to Performance Standards for Antimicrobial Disk Susceptibility Tests—Sixth Edition; Approved Standard, published by The National Committee for Clinical Laboratory Standards (NCCLS) guidelines; the minimum inhibitory concentration (MIC) is used to compare strains. Compounds are initially dissolved in dimethylsulfoxide (DMSO) as stock solutions.

| Strain Designation | Macrolide Resistance Mechanism(s) |
| --- | --- |
| *Staphylococcus aureus* 1116 | susceptible parent |
| *Staphylococcus aureus* 1117 | ermB |
| *Staphylococcus aureus* 0052 | susceptible parent |
| *Staphylococcus aureus* 1120 | ermC |
| *Staphylococcus aureus* 1032 | msrA, mph, esterase |
| *Staphylococcus hemolyticus* 1006 | msrA, mph |
| *Streptococcus pyogenes* 0203 | susceptible parent |
| *Streptococcus pyogenes* 1079 | ermB |
| *Streptococcus pyogenes* 1062 | susceptible parent |
| *Streptococcus pyogenes* 1061 | ermB |
| *Streptococcus pyogenes* 1064 | ermB |
| *Streptococcus agalactiae* 1024 | susceptible parent |
| *Streptococcus agalactiae* 1023 | ermB |
| *Streptococcus pneumoniae* 1016 | susceptible |
| *Streptococcus pneumoniae* 1046 | ermB |
| *Streptococcus pneumoniae* 1095 | ermB |
| *Streptococcus pneumoniae* 1175 | mefE |
| *Streptococcus pneumoniae* 0085 | susceptible |
| *Haemophilus influenzae* 0131 | susceptible |
| *Moraxella catarrhalis* 0040 | susceptible |
| *Moraxella catarrhalis* 1055 | erythromycin intermediate resistance |
| *Escherichia coli* 0266 | susceptible |

Assay II is utilized to test for activity against *Pasteurella multocida* and Assay III is utilized to test for activity against *Pasteurella haemolytica*.

ASSAY II

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 µl of dimethylsulfoxide (DMSO). Dilutions of the test compound are prepared using uninoculated BHI broth. The concentrations of the test compound used range from 200 µg/ml to 0.098 µg/ml by two-fold serial dilutions. The *P. multocida* inoculated BHI is diluted with uninoculated BHI broth to make a 104 cell suspension per 200 µl. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

ASSAY III

This assay is based on the agar dilution method using a Steers Replicator. Two to five colonies isolated from an agar plate are inoculated into BHI broth and incubated overnight at 37° C. with shaking (200 rpm). The next morning, 300 µl of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 µl of the *P. haemolytica* culture is inoculated onto BHI agar plates containing the various concentrations of the test compound using a Steers Replicator and incubated for 18 hours at 37° C. Initial concentrations of the test compound range from 100–200 µg/ml. The MIC is equal to the concentration of the test compound exhibiting 100% inhibition of growth of *P. haemolytica* as determined by comparison with an uninoculated control.

ASSAY IV

Murine *Staphylococcus aureus* Intraperitoneal Infection Model

Mice (female CF-1) are allotted to cages (10 per cage) upon their arrival, and allowed to acclimate for a minimum of 48 hours before being used. Mice are infected intraperitoneally with 0.5 ml of a 3 to 5×105 colony forming units (CFU)/ml log phase culture of *Staphylococcus aureus* strain UC 6097 in 5% hog gastric mucin. Each experiment has one infected, non-medicated control group. Generally, all mice in a given study can be challenged within 30 to 90 minutes, especially if a repeating syringe (such as a Cornwall® syringe) is used to administer the challenge culture. Thirty minutes after infection has begun, compound treatment is given. It may be necessary for a second person to begin compound dosing if all of the animals have not been challenged at the end of thirty minutes. Subcutaneous doses are administered into the loose skin in the back of the neck whereas oral doses are given by means of a feeding needle. In both cases, a volume of 0.2 ml is used per mouse. A control compound of known efficacy administered by the same route is included in each test. Animals are observed daily, and the number of survivors in each group is recorded for 72 hours (three days) post challenge. The PD50 is a calculated dose at which the compound tested protects 50% of a group of mice from mortality due to the bacterial infection which would be lethal in the absence of drug treatment.

ASSAY V

Murine *Staphylococcus aureus* Intramammary Infection Model

Lactating mice (female CF-1 that gave birth 2 to 5 days prior to the day of infection) (female CF-1) are allotted to cages (1 per cage) upon their arrival, and allowed to acclimate for 24–48 hours before being used. Mice are infected in the L4 mammary gland with 0.1 ml of a 300 to 450 colony forming units (CFU)/ml log phase culture of *Staphylococcus aureus* strain UC 6097. Each experiment has one infected, non-medicated control group. Thirty minutes after infection has begun, compound treatment is given. Subcutaneous doses are administered into the loose skin in the back of the neck whereas oral doses are given by means of a feeding needle. In both cases, a volume of 0.2 ml is used per mouse. The endpoint is the presence or absence of clinical mastitis symptoms and quantitation of bacterial numbers in the mammary glands five days after infection. Bacteria are quantitated by homogenizing the infected gland with 4 volumes of phosphate buffered saline for 30 seconds (Omni International, model TH). The homogenate and dilutions of the homogenate are plated on Brain Heart Infusion Agar, incubated at 37° C. overnight, and the colonies counted. The lower limit of detection is 50 CFU/gland. Infected, non-medicated mice have ~5×10 9 CFU/gland at the time of necropsy.

ASSAY VI

Determination of MIC of *Fusobacterium necrophorum* Isolated Using Anaerobic Plate Dilution Techniques Minimum inhibitory concentration (MIC) data may be collected from isolates of *Fusobacterium necrophorum* of cattle and sheep origin. The MIC values for *Fusobacterium necrophorum* are determined using plate dilution techniques and inoculation with a Steer's replicator. The procedures are those outlined in "Methods For Antimicrobial Susceptibility Testing Of Anaerobic Bacteria-Third Edition; Approved Standard" (vol. 13, no. 26, 1993) by the National Committee on Clinical Laboratory Standards (NCCLS). A total of 10 dilutions of the antimicrobials are tested as doubling dilutions of the drug (32 to 0.063 mcg/ml). Control strains of anaerobic bacteria (*Clostridium perfringens* ATCC 13124 and *Bacteroides fragilis* ATCC 25285) are used as controls on each inoculated plate.

The in vivo activity of the compounds of the present invention can be determined by conventional animal protection studies well known to those skilled in the art, usually carried out in rodents.

According to one in vivo model, mice are allotted to cages upon their arrival, and allowed to acclimate before being used. Animals are inoculated with a bacterial suspension (*P. multocida* strain 59A006) intraperitoneally. Each experiment has at least 3 non-medicated control groups including one infected with 0.1× challenge dose and two infected with 1× challenge dose; a 10× challenge data group may also be used. Generally, all mice in a given study can be challenged within 30–90 minutes, especially if a repeating syringe (such as a Cornwall® syringe) is used to administer the challenge.

Thirty minutes after challenging has begun, the first compound treatment is given.

The compounds of the present invention, and the pharmaceutically acceptable salts thereof (hereinafter "the active compounds"), may be adminstered through oral, parenteral, topical, or rectal routes in the treatment of bacterial and protozoal infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

In the treatment of cancer, in particular non-small cell lung cancer, the active compounds may be administered as described in European patent application publication number 758,549, published Feb. 2, 1997.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 99% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral adinistration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be adminstered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl-residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The following Examples further illustrate the method and intermediates of the present invention. It is to be understood that the present invention is not limited to the specific details of the Examples provided below.

TABLE 1

The compounds of Examples 1–142 have the general formula 6 as shown below with the R and Y substituents indicated in the table below. The compounds were prepared as described in the general preparations below. In the table, the yield and mass spectra (ms) data apply to the final product.

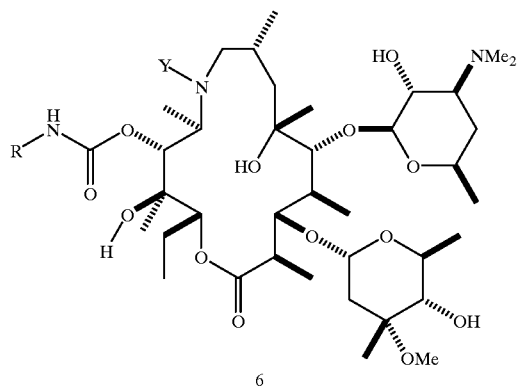 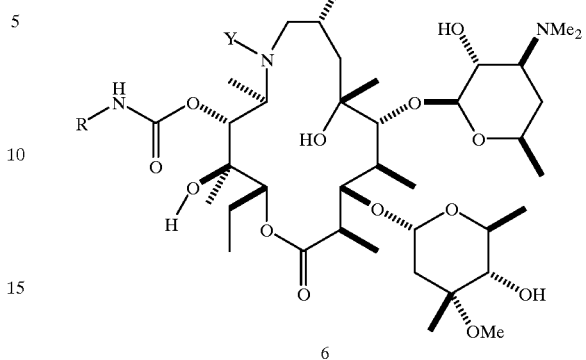

| Compounds | Y | R | MS | Yield |
|---|---|---|---|---|
| 1 | Me | 4-pyridylmethyl | 883.0 | 57 |
| 2 | H | 4-pyridylmethyl | 869.1 | 43 |
| 3 | Me | 2-pyridylmethyl | 883.6 | 34 |
| 4 | H | 2-pyridylmethyl | 869.1 | 24 |
| 5 | Me | 3-pyridylmethyl | 883.1 | 56 |
| 6 | H | 3-pyridylmethyl | 869.1 | 42 |
| 7 | Me | 4-pyridylethyl | 897.1 | 15.6 |
| 8 | H | 4-pyridylethyl | 883.1 | 40.0 |
| 9 | Me | 2-pyridylethyl | 897.1 | 66.7 |
| 10 | H | 2-pyridylethyl | 883.1 | 49.7 |
| 11 | Me | 3-pyridylethyl | 897.1 | 52.0 |
| 12 | H | 3-pyridylethyl | 883.1 | 40.3 |
| 13 | Me | 1-imidazolepropyl | 900.5 | 28.9 |
| 14 | H | 1-imidazolepropyl | 886.5 | 52.1 |
| 15 | Me | allyl | 832.5 | 79 |
| 16 | Me | n-propyl | 834.7 | 90 |
| 17 | Me | cyclopropyl | 832.7 | 30 |
| 18 | Me | methoxyethyl | 850.6 | 68 |
| 19 | Me | methoxypropyl | 864.6 | 82 |
| 20 | Me | benzyl | 882.6 | 70 |
| 21 | Me | n-hexyl | 876.8 | 87 |
| 22 | Me | N,N-ethylmethyl amine | 843.6 | 20 |
| 23 | H | allyl | 818.7 | 78 |
| 24 | H | methoxypropyl | 850.6 | 77 |
| 25 | H | n-propyl | 820.6 | 78 |
| 26 | H | n-butyl | 834.8 | 100 |
| 27 | H | methoxyethyl | 836.8 | 90 |
| 28 | H | N,N-ethylmethyl amine | 820.6 | 43 |
| 29 | Me | morpholino | 862.6 | |
| 30 | H | benzyl | 868.9 | 59 |
| 31 | H | cyclopropyl | 818.6 | 63 |
| 32 | H | cyclopentyl | 846.6 | |
| 33 | H | n-hexyl | 862.8 | |
| 34 | Me | n-butyl | 848.6 | 90 |
| 35 | Me | 2-fluorobenzyl | 900.3 | 14.1 |
| 36 | Me | 3-fluorobenzyl | 900.3 | 19.7 |
| 37 | Me | 4-fluorobenzyl | 900.3 | 27.2 |
| 38 | Me | 3,4-difluorobenzyl | 918.3 | 15.8 |
| 39 | Me | 3,5-difluorobenzyl | 918.3 | 17.8 |
| 40 | Me | 2,5-difluorobenzyl | 918.3 | 26.9 |
| 41 | Me | 2-trifluoromethylbenzyl | 950.2 | 35.5 |
| 42 | Me | 3-trifluoromethylbenzyl | 950.2 | 24.4 |
| 43 | Me | 4-trifluoromethylbenzyl | 950.2 | 41.0 |
| 44 | Me | furylmethyl | 872.2 | 38.3 |
| 45 | Me | 5-methyl furylmethyl | 886.5 | 39.5 |
| 46 | H | 2-fluorobenzyl | 886.2 | — |
| 47 | H | 3-fluorobenzyl | 886.2 | 26.5 |
| 48 | H | 3,4-difluorobenzyl | 904.2 | 21.6 |
| 49 | H | 2,5-difluorobenzyl | 904.2 | 19.2 |
| 50 | H | 3-trifluoromethylbenzyl | 936.2 | 21.4 |
| 51 | H | 4-trifluoromethylbenzyl | 936.2 | 37.3 |
| 52 | H | furylmethyl | 858.2 | 18.1 |
| 53 | H | 5-methyl furylmethyl | 872.2 | 32.8 |
| 54 | Me | piperonyl | 926.2 | 46.4 |
| 55 | H | 4-fluorobenzyl | 886.5 | 27.4 |
| 56 | H | 3,5-difluorobenzyl | 904.5 | 28.2 |
| 57 | H | 4-fluorophenethyl | 900.5 | 35.2 |
| 58 | H | 3-fluorophenethyl | 900.5 | 38.7 |
| 59 | H | 2-fluorophenethyl | 900.5 | 25.4 |
| 60 | Me | 2-fluorophenethyl | 914.7 | 27.1 |
| 61 | Me | 3-fluorophenethyl | 914.6 | 20.0 |
| 62 | Me | 4-fluorophenethyl | 914.6 | 22.0 |
| 63 | Me | ethyl | 821.0 | 78.6 |
| 64 | H | piperonyl | 912.5 | 50 |
| 65) | H | isopropyl | 820.5 | 28 |
| 66 | Me | 4-trifluoromethoxbenzyl | 966.7 | 84 |
| 67 | Me | 3-trifluoromethoxbenzyl | 966.7 | 19.1 |
| 68 | H | 3-trifluoromethoxbenzyl | 952.5 | 73.5 |
| 69 | H | 4-trifluoromethoxbenzyl | 952.5 | 18.1 |
| 70 | Me | 4-pyridylcarbonyl-aminoethyl | 940.3 | 36.7 |
| 71 | Me | isopropyl | 834.7 | 71.7 |
| 72 | H | thiophenemethyl | 874.7 | 15.5 |
| 73 | Me | aminoethyl | 835.7 | 87.5 |
| 74 | Me | 2-methoxybenzyl | 912.2 | 22.3 |
| 75 | Me | 4-methoxybenzyl | 912.2 | 16.4 |
| 76 | Me | 3,4-dimethylbenzyl | 942.21 | 19 |
| 77 | Me | 4-methylbenzyl | 896.2 | 23.9 |
| 78 | Me | 2,4-dimethylbenzyl | 910.2 | 6.4 |
| 79 | Me | 3-methylbenzyl | 896.2 | 14.7 |
| 80 | Me | 3-aminomethyl benzyl | 911.2 | 36.9 |
| 81 | Me | 4-methoxyphenethyl | 926.2 | 45.6 |
| 82 | Me | 2,5-dimethoxyphenethyl | 956.2 | 8.1 |
| 83 | Me | 2-methoxyphenethyl | 926.2 | 20.9 |
| 84 | Me | 2,3-dimethoxyphenethyl | 956.2 | 19 |
| 85 | Me | 3,4-dimethoxyphenethyl | 956.2 | 14.8 |
| 86 | Me | 2-ethoxyphenethyl | 940.3 | 4.7 |
| 87 | H | 4-ethoxyphenethyl | 926.2 | 43.3 |
| 88 | H | 2,3-dimethoxyphenethyl | 942.2 | 39.2 |
| 89 | H | 3,4-dimethylbenzyl | 928.2 | 45 |
| 90 | H | 2-ethoxyphenethyl | 926.3 | 28.9 |
| 91 | Me | 4-ethoxyphenethyl | 940.3 | 30.7 |
| 92 | H | 2,3-dimethoxyphenethyl | 942.3 | 34.8 |
| 93 | H | 3,5-dimethoxyphenethyl | 942.3 | 32.0 |
| 94 | H | 2,4-dimethylbenzyl | 896.0 | 37.9 |
| 95 | H | 4-phenylbutyl | 910.2 | 39.2 |
| 96 | H | 3-phenylpropyl | 896.2 | 41.1 |
| 97 | H | 4-methoxybenzyl | 898.2 | 53 |
| 98 | H | 2-methoxybenzyl | 898.2 | 42 |
| 99 | H | 3-chlorobenzyl | 902.6 | 41 |
| 100 | H | 2,4-dichlorobenzyl | 937 | 33 |
| 101 | H | 3,4-dichlorobenzyl | 937 | 39 |
| 102 | H | 4-methylbenzyl | 882.1 | 53 |
| 103 | H | 2,5-dimethoxybenzyl | 928.1 | 50 |
| 104 | H | 4-chlorobenzyl | 902.6 | 42 |
| 105 | Me | 4-phenbutyl | 924.2 | 23.7 |
| 106 | H | 2-methoxyphenethyl | 912.5 | 36.3 |
| 107 | H | 2,3-dimethoxybenzyl | 928.2 | 25.0 |
| 108 | H | 3-chlorophenethyl | 916.6 | 38.7 |
| 109 | Me | 2,3-dimethoxybenzyl | 942.2 | 22.3 |
| 110 | Me | 3-chlorophenethyl | 930.6 | 20.4 |
| 111 | Me | 4-chlorophenethyl | 930.7 | 11.3 |
| 112 | Me | 4-methylphenethyl | 910.2 | 26.3 |
| 113 | Me | 3,4-dichlorophenethyl | 965.1 | 6.7 |

-continued

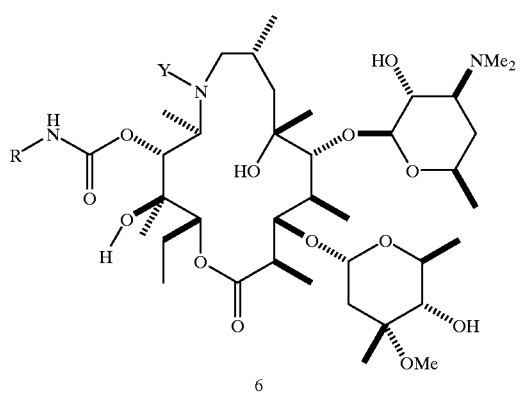

| Compounds | Y | R | MS | Yield |
|---|---|---|---|---|
| 114 | Me | 3,5-dimethoxyphenethyl | 956.2 | 27.0 |
| 115 | Me | 2,4-dichlorophenethyl | 965.1 | 9.3 |
| 116 | Me | 3-phenpropyl | 910.2 | 30.2 |
| 117 | H | 4-chlorophenethyl | 916.6 | 30.6 |
| 118 | H | 3,4-dichlorophenethyl | 951.1 | 4.2 |
| 119 | Me | N-penzylpiperazinyl | 951.3 | 6.1 |
| 120 | H | 2,2-diphenethyl | 972.3 | 22.5 |
| 121 | H | ethyl-(2,3-dimethoxyphenyl)-indole | 1057 | 28.7 |
| 122 | Me | ethyl-(2,3-dimethoxyphenyl)-indole | 1071 | 15.2 |
| 123 | H | 3-ethoxy-2-hydroxyphenethyl | 942.2 | 14.7 |
| 124 | H | 4-methylphenethyl | 896.2 | 20.3 |
| 125 | Me | 4-chlorophenethyl | 916.6 | 12.4 |
| 126 | Me | 2,2-diphenylethyl | 986.3 | 15.3 |
| 127 | H | 3-methylbenzyl | 882.2 | 28.6 |
| 128 | H | 2,4-dichlorophenethyl | 951.1 |  |
| 129 | Me | 3-ethoxy-4-hydroxyphenethyl | 956.3 | 9.3 |
| 130 | H | 4-methoxyphenethyl | 912.2 | 36.5 |
| 131 | Me | 3-chlorobenzyl | 916.6 | 20.2 |
| 132 | H | 3-methoxy-4-hydroxyphenethyl | 928.2 | 18.4 |
| 133 | Me | 3,4-dichlorobenzyl | 951.1 | 22.8 |
| 134 | Me | 4-hydroxyphenethyl | 912.2 | 8.8 |
| 135 | Me | 4-aminophenethyl | 911.2 | 8.7 |
| 136 | H | 4-hydroxy-phenethyl | 898.2 | 9.8 |
| 137 | Me | 4-ethylphenethyl | 924.2 | 24.9 |
| 138 | Me | 4-bromophenethyl | 974.0 | 27.7 |
| 139 | H | 2,5-dibenzyloxyphenethyl | 1093 | 1.3 |
| 140 | Me | ethynyl | 816.1 |  |
| 141 | H | 4-ethylphenethyl | 910.2 | 11.3 |
| 142 | H | 4-bromophenethyl | 961.1 | 10.8 |

General Methods for Preparation of Examples 1–142 in Table 1

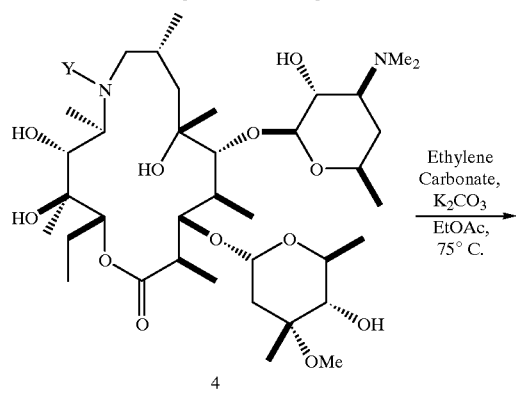

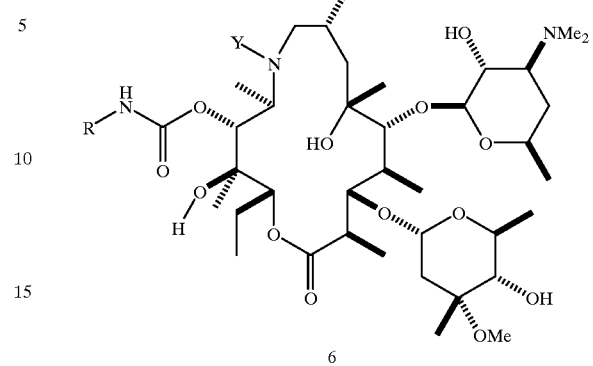

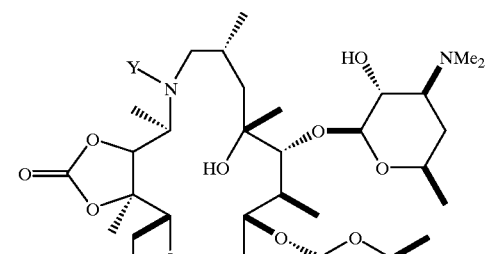

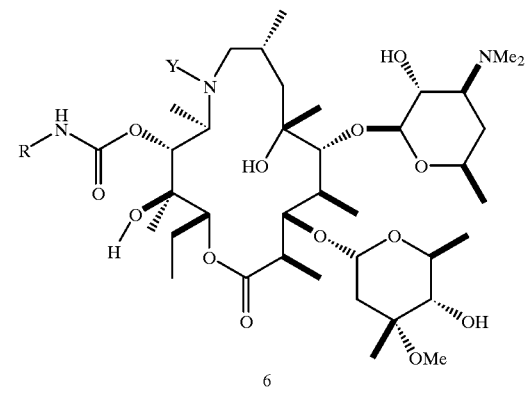

Preparation of 11, 12-carbonate (5): Azalide derivatives (4) (5 g) were dissolved in EtOAc (75 mL), followed by the addition of ethylene carbonate (5 eq) and $K_2CO_3$ (1 eq). The resulting solution was stirred at 75° C. for two to five days. Solid $K_2CO_3$ was first removed by filtration, and the organic layer was extracted with pH 6.0 buffer. To the aqueous layer was added saturated $NaHCO_3$ solution until pH is greater than 8, and the crude product was extracted with $CH_2Cl_2$ (2×100 mL). The organic layer was dried ($Na_2SO_4$), and solvent removed in vacuo to give the crude product which was purified by flash chromatography using 3% MeOH and 0.5% ammonia in $CH_2Cl_2$.

Preparation of 11-carbamate (6): 11,12-carbonate of azilide (5) (250 mg~760 mg) was dissolved in the amine (1~2 mL), catalytic amount of pyridine hydrochloride was added when small aliphalic amines were used, N—Me-imidazole was used as both a solvent and catalyst when lipophilic aromatic amines such as fluorobenzyl amine were used, and neither pyridine hydrochloride nor N—Me-imidazole was added when heterocyclic aromatic amines were used, and the resulting solution was stirred at 23° C. for two to five days. The reaction mixture was then taken up into CH$_2$Cl$_2$ (50~150 mL), and washed with water or 0.5 M ph 7.0 sodium phosphate buffer (5×50~150 mL) to remove the unreacted amine. The organic layer was then washed with brine (50 mL) and dried (Na$_2$SO$_4$). The solvent was then removed in vacuo to give the crude product which was then purified by flash chromatography using 7:2:1 of hexane4EtOAc/Et$_2$NH or 3% MeOH and 0.5% ammonia in CH$_2$Cl$_2$ to give the product.

TABLE 2

The compounds of Examples 143–151 have the general formula 9 below with the R substituents indicated in the table below.

The compounds were prepared as described in general preparations below.

In the table, the yield and mass spectra (Ms) data apply to the final product.

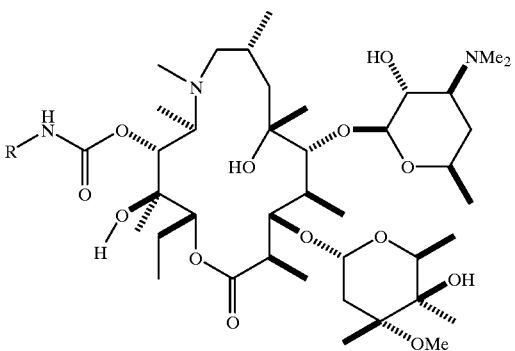

9

| Compounds | R | MS | Yield |
|---|---|---|---|
| 143 | 3-Pyridylmethyl amine | 897.1 | 44.6 |
| 144 | 4-Pyridylmethyl amine | 897.1 | 33.5 |
| 145 | 2-Pyridylmethyl amine | 897.1 | 40.4 |
| 146 | 3-Pyridylethyl amine | 911.7 | 52.9 |
| 147 | 4-Pyridylethyl amine | 911.7 | 36.7 |
| 248 | 2-Pyridylethyl amine | 911.7 | 22.9 |
| 149 | 2-Furylmethyl amine | 886.5 | 13.5 |
| 150 | 5-methyl-2-furylmethyl amine | 900.2 | 4.4 |
| 151 | 2-thiophenemethyl amine | 902.4 | 30 |

General Methods for Preparation of Examples 143–151 in Table 2

TABLE 2-continued

The compounds of Examples 143–151 have the general formula 9 below with the R substituents indicated in the table below.

The compounds were prepared as described in general preparations below.

In the table, the yield and mass spectra (Ms) data apply to the final product.

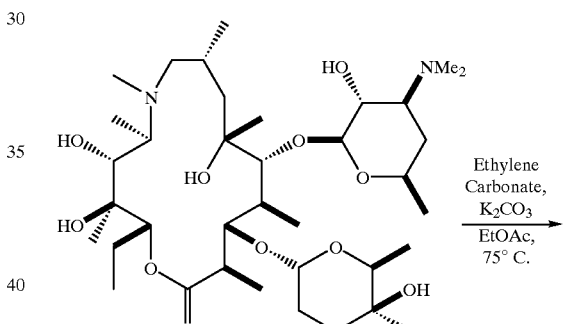

9

Compounds    R    MS    Yield

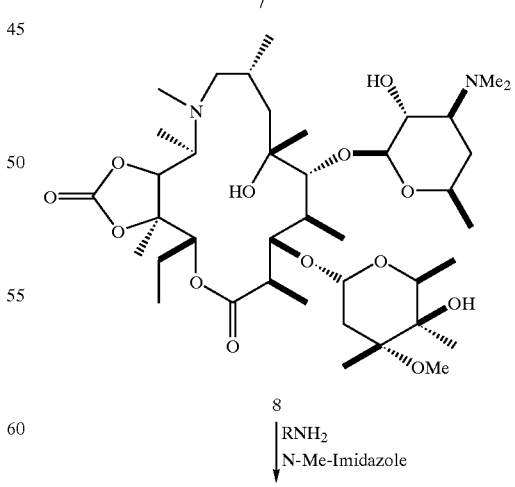

TABLE 2-continued

The compounds of Examples 143–151 have the general formula 9 below with the R substituents indicated in the table below.
The compounds were prepared as described in general preparations below.
In the table, the yield and mass spectra (Ms) data apply to the final product.

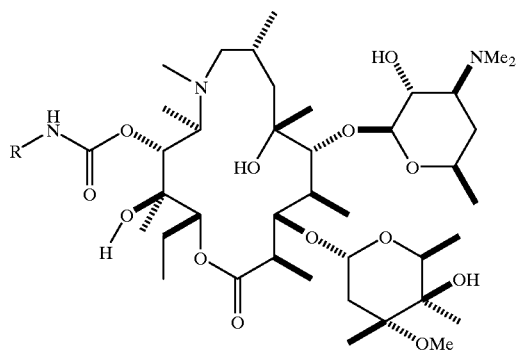

9

| Compounds | R | MS | Yield |
|---|---|---|---|

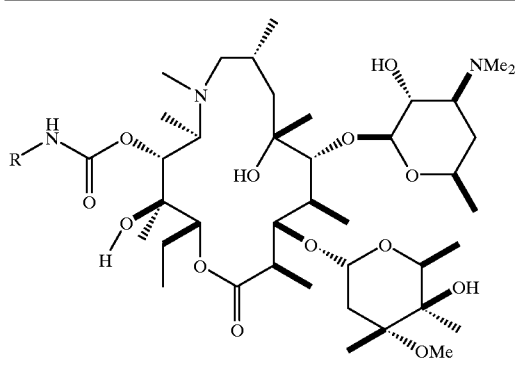

9

Preparation of 4"-tert-Alcohol carbonate (8): 4"-tert-Alcohol azalide (7) (1 g, 1.31 mmol), ethylene carbonate (700 mg, 7.95 mmol) and $K_2CO_3$ (215 mg, 1.56 mmol) were mixed in a round bottom flask, followed by the addition of EtOAc (15 mL). The resulting solution was heated to 75° C. for 48 h. Solid $K_2CO_3$ was filtered off, and the filtrate was diluted with EtOAc (50 mL). The organic layer was washed with water (3×50 ml), and dried ($Na_2SO_4$), and solvent was removed in vacuo to give the product, 860 mg (83%).

Preparation of 4"-tert-Alcohol Carbamate (9): 4"-tert-alcohol carbonate (8) (250 mg~760 mg) was dissolved in the amine (1~2 mL), and the resulting solution was stirred at 23° C. for two to five days. The reaction mixture was then taken up into $CH_2Cl_2$ (50~150 mL), and washed with water or 0.5 M pH 7.0 sodium phosphate buffer (5×50~150 mL) to remove the unreacted amine. The organic layer was then washed with brine (50 mL) and dried ($Na_2SO_4$). The solvent was then removed in vacuo to give the crude product which was then purified by flash chromatography using 7:2:1 of hexane/EtOAc/$Et_2NH$ to give the product.

TABLE 3

The compounds of Examples 152–154 have the general formula 12 below with the R substituents indicated in the table below.
The compounds were prepared as described in Preparations below.
In the table, the yield and mass spectra (ms) data apply to the final product.

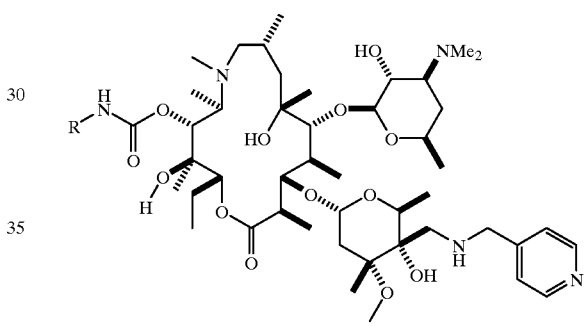

12

| Compounds | R | MS | Yield |
|---|---|---|---|
| 152 | 3-Pyridylmethyl | 1003.8 | 47.9 |
| 153 | 4-Pyridylmethyl | 1003.8 | 50.4 |
| 154 | 2-methoxyethyl | 970.6 | 45.4 |

General Methods for Preparation of Examples 152-154 in Table 3

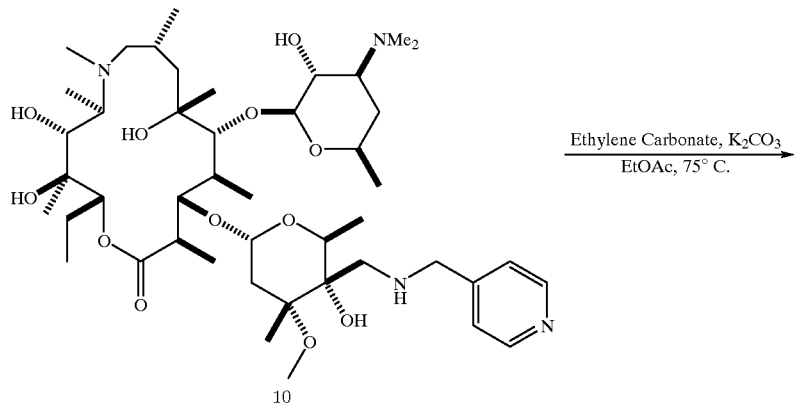

10

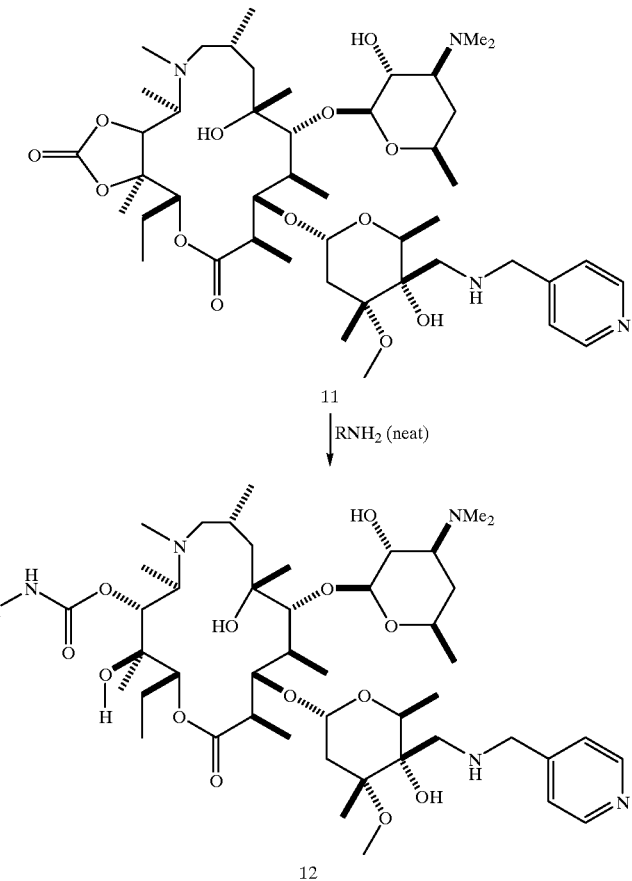

Preparation of 4"-tert-Amino Alcohol carbonate (11): 4"-tert-Amino alcohol azalide (10) (1 g, 1.31 mmol), ethylene carbonate (700 mg, 7.95 mmol) and $K_2CO_3$ (215 mg, 1.56 mmol) were mixed in a round bottom flask, followed by the addition of EtOAc (15 mL). The resulting solution was heated to 75° C. for 48 h. Solid $K_2CO_3$ was filtered off, and the filtrate was diluted with EtOAc (50 mL). The organic layer was washed with water (3×50 ml), and dried ($Na_2SO_4$), and solvent was removed in vacuo to give the product, 860 mg (83%).

Preparation of 4"-tert-Amino Alcohol Carbamate (12): 4"-tert-amino alcohol carbonate (11) ( 250 mg~760 mg) was dissolved in the amine (1~2 mL), and the resulting solution was stirred at 23° C. for two to five days. The reaction mixture was then taken up into $CH_2Cl_2$ (50~150 mL), and washed with water to remove the unreacted amine. The organic layer was then washed with brine (50 mL) and dried ($Na_2SO_4$). The solvent was then removed in vacuo to give the crude product which was then purified by flash chromatography sing 7:2:1 of hexane/EtOAc/$Et_2NH$ to give the product.

TABLE 4

The compounds of Examples 155–215 have the general formula 15 below with the R substituents indicated in the table below. The compounds were prepared as described in Preparations below. In the table, the yield and mass spectra (ms) data apply to the final product.

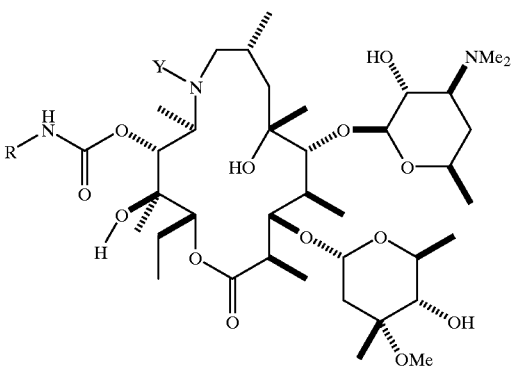

| Compounds | Y | R | MS | Yield |
|---|---|---|---|---|
| 155 | ethyl | 2-pyridylmethyl | 897.3 | 38.7 |
| 156 | ethyl | 3-pyridylmethyl | 897.2 | 50.7 |
| 157 | ethyl | 4-pyridylmethyl | 897.3 | 35.2 |
| 158 | propyl | 2-pyridylmethyl | 911.2 | 48.2 |
| 159 | propyl | 3-pyridylmethyl | 911.2 | 43.0 |
| 160 | propyl | 4-pyridylmethyl | 911.2 | 45.8 |
| 161 | cyclopropylmethyl | 2-pyridylethyl | 923.2 | 44.5 |
| 162 | cyclopropylmethyl | 2-pyridylmethyl | 937.2 | 30.9 |
| 163 | cyclopropylmethyl | 3-pyridylmethyl | 923.2 | 29.0 |
| 164 | cyclopropylmethyl | 3-pyridylethyl | 937.2 | 45.7 |
| 165 | cyclopropylmethyl | 4-pyridylmethyl | 923.2 | 46.6 |

-continued

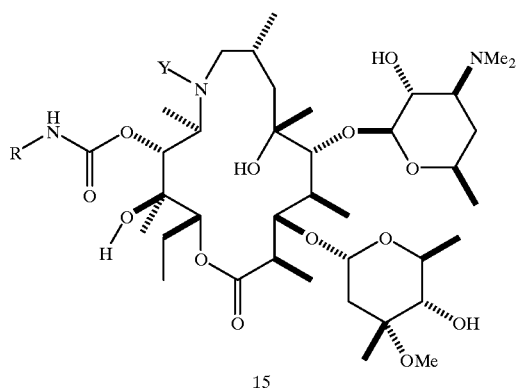

| Compounds | Y | R | MS | Yield |
|---|---|---|---|---|
| 166 | cyclopropylmethyl | 4-pyridylethyl | 937.3 | 46.0 |
| 167 | butyl | 2-pyridylmethyl | 925.6 | 78.4 |
| 168 | butyl | 3-pyridylmethyl | 925.6 | 71.0 |
| 169 | butyl | 4-pyridylmethyl | 925.6 | 76.3 |
| 170 | 4-pyridylmethyl | 1-imidazolepropyl | 977.5 | 49.1 |
| 171 | 4-pyridylmethyl | 3-pyridylmethyl | 960.5 | 36.7 |
| 172 | 4-pyridylmethyl | 4-pyridylmethyl | 960.5 | 30.6 |
| 173 | cyclopropylmethyl | 1-imidazolepropyl | 940.6 | 70.1 |
| 174 | butyl | 1-imidazolepropyl | 942.6 | 75.3 |
| 175 | butyl | 2-pyridylethyl | 939.1 | 82.2 |
| 176 | butyl | 3-pyridylethyl | 939.1 | 88.2 |
| 177 | butyl | 4-pyridylethyl | 939.1 | 82.9 |
| 178 | pentyl | 2-pyridylmethyl | 939.1 | 22.6 |
| 179 | pentyl | 3-pyridylmethyl | 939.1 | 29.3 |
| 180 | pentyl | 4-pyridylmethyl | 939.1 | 25.8 |
| 181 | hexyl | 2-pyridylmethyl | 953.2 | 18.4 |
| 182 | hexyl | 3-pyridylmethyl | 953.2 | 22.0 |
| 183 | hexyl | 4-pyridylmethyl | 953.2 | 28.4 |
| 184 | 3-phenylpropyl | 2-pyridylmethyl | 987.1 | 42.9 |
| 185 | 3-phenylpropyl | 3-pyridylmethyl | 987.1 | 71.1 |
| 186 | 3-phenylpropyl | 4-pyridylmethyl | 987.1 | 35.7 |
| 187 | heptyl | 2-pyridylmethyl | 967.2 | 82.6 |
| 188 | heptyl | 3-pyridylmethyl | 967.2 | 91.1 |
| 189 | heptyl | 4-pyridylmethyl | 967.2 | 53.0 |
| 190 | octyl | 2-pyridylmethyl | 981.2 | 97.5 |
| 191 | octyl | 3-pyridylmethyl | 891.2 | 81.9 |
| 192 | octyl | 4-pyridylmethyl | 981.2 | 47.7 |
| 193 | nonyl | 2-pyridylmethyl | 995.6 | 82.5 |
| 194 | nonyl | 3-pyridylmethyl | 995.7 | 86.8 |
| 195 | nonyl | 4-pyridylmethyl | 995.6 | 52.9 |
| 196 | 3-thiomethyl propyl | 2-pyridylmethyl | 957.5 | 89.3 |
| 197 | 3-thiomethyl propyl | 3-pyridylmethyl | 957.4 | 87.1 |
| 198 | 3-thiomethyl propyl | 4-pyridylmethyl | 957.4 | 88.0 |
| 199 | 4-pentenyl | 2-pyridylmethyl | 937.4 | 29.3 |
| 200 | 4-pentenyl | 3-pyridylmethyl | 937.4 | 38.2 |
| 201 | 4-pentenyl | 4-pyridylmethyl | 937.3 | 30.7 |
| 202 | 3-methyl butyl | 2-pyridylmethyl | 939.1 | 44.2 |
| 203 | 3-methyl butyl | 3-pyridylmethyl | 939.2 | 60.4 |
| 204 | 3-methyl butyl | 4-pyridylmethyl | 939.2 | 55.8 |
| 205 | 2-phenethyl | 2-pyridylmethyl | 973.1 | 37.3 |
| 206 | 2-phenethyl | 3-pyridylmethyl | 973.1 | 15.1 |
| 207 | 2-phenethyl | 4-pyridylmethyl | 973.1 | 13.8 |
| 208 | phenylpropargyl | 2-pyridylmethyl | 983.1 | 27.6 |
| 209 | phenylpropargyl | 3-pyridylmethyl | 983.1 | 23.6 |
| 210 | phenylpropargyl | 4-pyridylmethyl | 983.1 | 37.8 |
| 211 | propyl | 2-phenoxy ethyl | 940.1 | 30.4 |
| 212 | butyl | 2-phenoxy ethyl | 954.2 | 40.8 |
| 213 | propyl | 2-pyridylethyl | 925.2 | 31.3 |
| 214 | propyl | 3-pyridylethyl | 925.2 | 37.5 |
| 215 | propyl | 4-pyridylethyl | 925.2 | 26.7 |

-continued

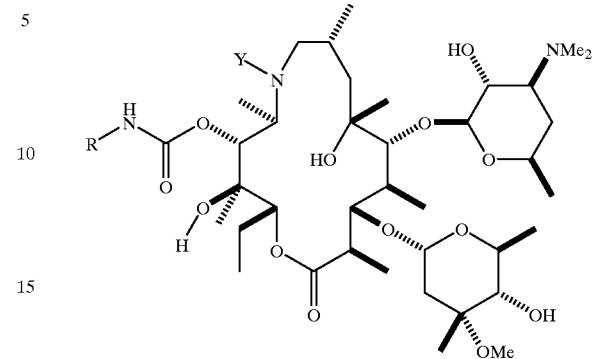

| Compounds | Y | R | MS | Yield |
|---|---|---|---|---|

General Methods for Preparation of Examples 155–215 in Table 4

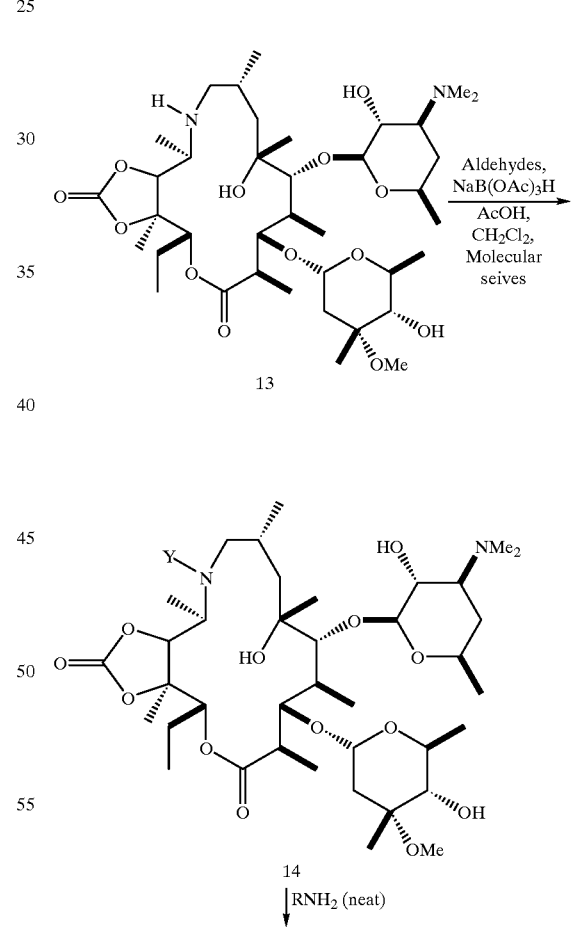

-continued

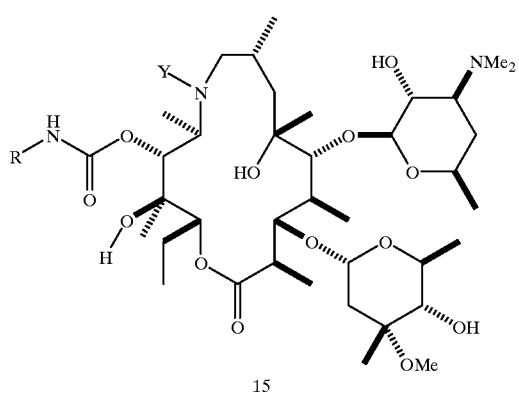

| Compounds | Y | R | MS | Yield |
|---|---|---|---|---|

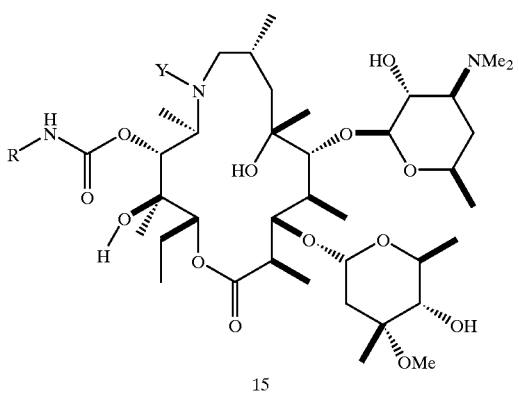

Preparation of 9N-Modified Azalide 11,12-Carbonate (14): N-desmethyl azithromycin 11,12-carbonate (13) (2 g, 2.63 mmol) and the aldehyde (13.2 mmol) were dissolved in $CH_2Cl_2$ (25 mL), followed by the addition of AcOH (0.448 mL, 7.89 mmol) and monecular sieves (3 A, 5 g). After the mixture was stirred at room temperature for 10~15 min, $NaB(OAc)_3H$ (2.80 g, 13.2 mmol) was added, and the stirring was continued for 24 h. The reaction was first quenched with $NaHCO_3$, then diluted with $CH_2Cl_2$. The organic layer was washed with saturated $NaHCO_3$ (50 mL), brine (50 mL), and dried ($Na_2SO_4$). The solvent was then removed in vacuo to give the product, which was pure enough for the next step of the sequence.

Synthesis of 9N-Alkylated 11-Carbamate Azalides (15): 11,12-carbonate of 9N-modified azalide (14) (250 mg~760 mg) was dissolved in the amine (1~2 mL), and the resulting solution was stirred at 23° C. for two to five days. The reaction mixture was then taken up into $CH_2Cl_2$ (50~150 mL), and washed with water to remove the unreacted amine. The organic layer was then washed with brine (50 mL) and dried ($Na_2SO_4$). The solvent was then removed in vacuo to give the crude product which was then purified by flash chromatography using 7:2:1 of hexane/EtOAc/$Et_2NH$ or 3% MeOH and 0.5% ammonia in $CH_2Cl_2$ to give the product.

TABLE 5

The compounds of Examples 216–217 have the general formula 18 below with the R substituents indicated in the table below.
The compounds were prepared as described in Preparations below. In the table, the yield and mass spectra (ms) data apply to the final product.

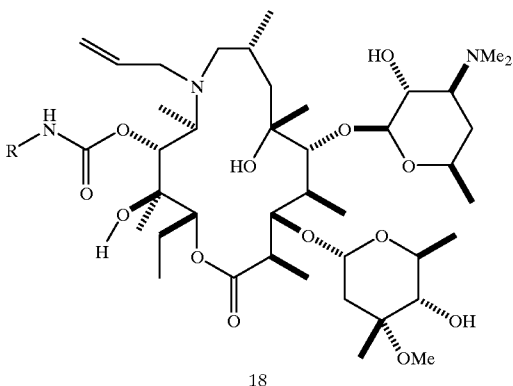

| Compounds | R | MS | Yield |
|---|---|---|---|
| 216 | 3-Pyridylmethyl | 909.4 | 5.0 |
| 217 | 4-Pyridylmethyl | 909.6 | 9.5 |

General Methods for Preparation of Examples 1–2 in Table 5

TABLE 5-continued

The compounds of Examples 216–217 have the general formula 18 below with the R substituents indicated in the table below.
The compounds were prepared as described in Preparations below. In the table, the yield and mass spectra (ms) data apply to the final product.

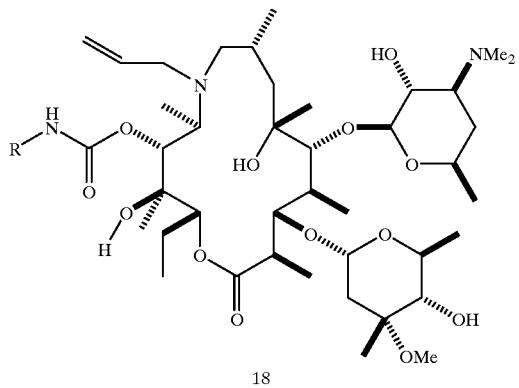

18

| Compounds | R | MS | Yield |
|---|---|---|---|

Preparation of N-desmethyl-N-allyl-azithromycin (16): N-desmethyl-azithromycin (13) (10 g, 11.5 mmol) was dissolved in toluene (100 mL), followed by the addition of Et$_3$N, allyl acetate and Pd(Ph$_3$)$_4$, the resulting solution was stirred at 80° C. for 7 h and then room temperature overnight. The solvent was then removed in vacuo and the product was was purified by flash chromatography using 2% MeOH and 0.2% ammonia in CH$_2$Cl$_2$ to give 5.1 g product, 49%.

Preparation of 9N-allyl-11, 12-carbonate of azithromycin (17): Azalide derivatives (16) (3.7 g, 4.8 mmol) was dissolved in EtOAc (75 mL), followed by the addition of ethylene carbonate (23.8 g, 27.0 mmol) and $K_2CO_3$ (0.7 g, 4.2 mmol). The resulting solution was stirred at 75° C. for three days. Solid $K_2CO_3$ was first removed by filtration, and the organic layer was extracted with pH 6.0 buffer. To the aqueous layer was added saturated $NaHCO_3$ solution until pH is greater than 8, and the crude product was extracted with $CH_2Cl_2$ (2×100 mL). The organic layer was dried ($Na_2SO_4$), and solvent removed in vacuo to give the product, >99% yield.

Preparation of 9N-allyl 11-carbamate azalide (18): 11,12-carbonate of N-allyl azilide (17) ( 250 mg~760 mg) was dissolved in the amine (1~2 mL), and the resulting solution was stirred at 23° C. for two to five days. The reaction mixture was then taken up into EtOAc (50~150 mL), and washed with water to remove the unreacted amine. The organic layer was then washed with brine (50 mL) and dried ($Na_2SO_4$). The solvent was then removed in vacuo to give the crude product which was then purified by flash chromatography using 7:2:1 of hexane/EtOAc/$Et_2NH$ or 3% MeOH and 0.5% ammonia in $CH_2Cl_2$ to give the product.

We claim:

1. A compound of the formula

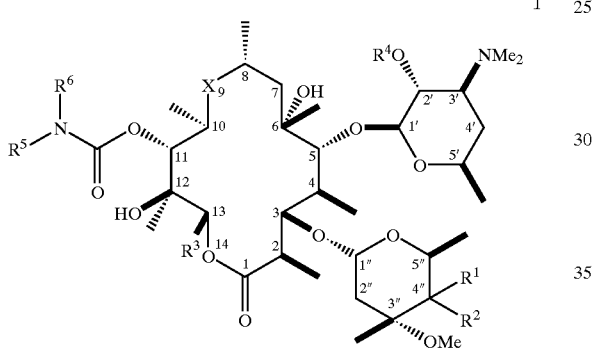

or a pharmaceutically acceptable salts thereof, wherein:

X is —$CH_2NR^7$—, or —$NR^7CH_2$— wherein the first dash of each of the foregoing X groups is attached to C-10 carbon of the compound of formula 1 and the last dash of each group is attached to the C-8 carbon of the compound of formula 1;

$R^1$ is hydroxy;

$R^2$ is H, $C_1$–$C_{10}$alkyl, $C_2$–$C_{10}$-alkenyl, $C_2$–$C_{10}$ alkynyl, cyano, —$CH_2S(O)_nR^8$ wherein n is an integer ranging from 0 to 2, —$CH_2R^8$, —$CH_2ONR^8R^9$, —$(CH_2)_m$($C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^1$ groups are optionally substituted by 1 to 3 substituents independently selected from the groups consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy $C_1$–$C_6$ alkyl, $C_1$–$C_6$ alkoxy, $C_6$–$C_{10}$ aryl, and 5–10 membered heteroaryl;

$R^3$ is an $C_2$–$C_8$ alkyl, alkenyl, alkynyl, alkoxyalkyl or alkylthioalkyl group any of which may optionally be substituted by one or more hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one or more hydroxyl or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms;

Or $R^3$ is phenyl which may be optionally substituted with at least one substituent selected from $C_1$–$C_4$ alkyl, $C_1$–$C_4$ alkoxy and $C_1$–$C_4$ alkylthio groups, halogen atoms, hydroxyl groups, trifluoromethyl, and cyano;

$R^4$ is H or a hydroxy protecting group;

each $R^5$ and $R^6$ is independently H, $C_1$–$C_{10}$ alkyl, $C_2$–$C_{10}$ alkenyl, $C_2$–$C_{10}$ alkynyl, —$(CH_2)_mC_6$–$C_{10}$ aryl, —$(CH_2)_m$(5–10 membered heteroaryl), wherein m is an integer ranging from 0 to 4, and wherein the alkyl, alkenyl, aryl, heteroaryl and alkynyl moieties of the foregoing $R^5$ and $R^6$ groups are optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl, and 5–10 membered heteroaryl; or $R^5$ and $R^6$ may be taken together to form a 4–7 membered saturated ring or a 5–10 membered heteroaryl ring, wherein said saturated and heteroaryl rings optionally include 1 or 2 heteroatoms selected from O, S, and N, in addition to the nitrogen to which $R^5$ and $R^6$ are attached, said saturated ring optionally includes 1 or 2 carbon-carbon double or triple bonds, and said saturated and heteroaryl rings are optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl, and 5–10 membered heteroaryl;

$R^7$ is H, $C_1$–$C_{10}$ alkyl, $C_2$–$C_{10}$ alkenyl, $C_2$–$C_{10}$ alkynyl, —$(CH_2)_mC_6$–$C_{10}$ aryl, —$(CH_2)_m$(5–10 membered heteroaryl), wherein m is an integer ranging from 0 to 4, and wherein the alkyl, alkenyl, aryl, heteroaryl and alkynyl moieties of the foregoing $R^5$ and $R^6$ groups are optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl, and 5–10 membered heteroaryl;

each $R^8$ and $R^9$ is independently H, hydroxy, $C_1$–$C_6$ alkoxy, $C_1$–$C_6$ alkyl, $C_2$–$C_6$ alkenyl, $(CH_2)_m(C_6$–$C_{10}$ ) aryl, $(CH_2)_m$(5–10 membered heteroaryl), wherein m is an integer ranging from 0 to 4, or $C_2$–$C_{10}$ alkylyl; and Me is methyl.

2. The compound of claim 1 wherein $R^1$ is OH.

3. The compound of claim 2 wherein $R^2$ is hydrogen or methyl $R^3$ is ethyl, $R^4$ is H and $R^5$ is H.

4. The compound of claim 3 wherein $R^6$ is $C_1$–$C_{10}$ alkyl, $C_2$–$C_{10}$ alkenyl, $C_2$–$C_{10}$ alkynyl, or $(CH_2)_m$ $C_6$–$C_{10}$ aryl wherein m is an interger ranging from 0 to 4 and wherein the alkyl, alkenyl, alkynyl, and aryl moieties of the said $R^6$ group are optionally substituted by 1 to 3 substituents independently selected from the group consisting of halo, cyano, nitro, trifluoromethyl, azido, hydroxy, $C_1$–$C_6$ alkyl and $C_1$–$C_6$ alkoxy.

5. The compound of claim 3 wherein $R^6$ is —$(CH_2)_m$(5–10 membered heteroaryl) wherein m is an interger ranging from 0 to 4 and wherein the heteroaryl moieties of the said $R^6$ group are optionally substituted by 1 to 3 substituents independently selected from the group consisting of halo, cyano, nitro, trifluoromethyl, azido, hydroxy, $C_1$–$C_6$ alkyl $C_1$–$C_6$ alkoxy.

6. The compound of claim 5 wherein $R^6$ is 2-pyridylmethyl, 3-pyridylmethyl, 4-pyridylmethyl, 2-pyridylethyl, 3-pyridylethyl, 4-pyridylethyl, 2-fluorobenzyl, 3-fluorobenzyl, 4-fluorobenzyl, 2,3-dimethoxybenzyl, 2,4-dimethoxybenzyl, 2,5-dimethoxybenzyl, 2,6-dimethoxybenzyl, 3,4-dimethoxybenzyl, 3,5-dimethoxybenzyl, 3,6-dimethoxybenzyl, 3,4-dimethoxyphenylethyl, allyl, propyl or isopropyl.

7. A pharmaceutical composition for the treatment of a bacterial infection or a protozoa infection in a mammal, fish or bird which comprises a therapeutcally effective amount of a compound of formula 1 and a pharmaceutically acceptable carrier.

8. A method of treating a bacterial infection or a protozoa infection in a mammal, fish or bird which comprises administering to said mammal, fish or a bird a therapeutically effective amount of a compound of claim 1.

9. A method of preparing a compound of the formula

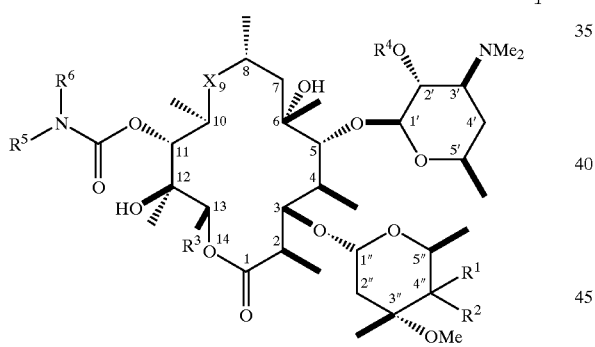

1 or a pharmaceutically acceptable salt thereof, wherein:

X is —$CH_2NR^7$—, or —$NR^7CH_2$— wherein the first dash of each of the foregoing X groups is attached to C-10 carbon of the compound of formula 1 and the last dash of each group is attached to the C-8 carbon of the compound of formula 1;

$R^1$ is hydroxy;

$R^2$ is H, $C_1$–$C_{10}$ alkyl, $C_2$–$C_{10}$-alkenyl, $C_2$–$C_{10}$ alkynyl, cyano, —$CH_2S(O)_nR^8$ wherein n is an integer ranging from 0 to 2, —$CH_2OR^8$, —$CH_2NR^8R^9$, —$(CH_2)_m$($C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^1$ groups are optionally substituted by 1 to 3 substituents independently selected from the group consisting of halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and 5–10 membered heteroaryl;

$R^3$ is an $C_2$–$C_8$ alkyl, alkenyl, alkynyl, alkoxyalkyl or alkylthioalkyl group any of which may optionally be substituted by one or more hydroxyl groups; a $C_5$–$C_8$ cycloalkylalkyl group wherein the alkyl group is an alpha-branched $C_2$–$C_8$ alkyl group; a $C_3$–$C_5$ cycloalkyl or $C_5$–$C_8$ cycloalkenyl group, either of which may optionally be substituted by methyl or one or more hydroxyl or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms;

Or $R^3$ is phenyl which may be optionally substituted with at least one substituent selected from the group consisting of $C_1$–$C_4$ alkyl, $C_1$–$C_4$ alkoxy and $C_1$–$C_4$ alkylthio groups, halogen atoms, hydroxyl groups, trifluoromethyl, and cyano;

$R^4$ is H or a hydroxy protecting group;

each $R^5$ and $R^6$ is independently H, $C_1$–$C_{10}$ alkyl, $C_2$–$C_{10}$ alkenyl, $C_2$–$C_{10}$ alkynyl, —$(CH_2)_mC_6$–$C_{10}$ aryl, —$(CH_2)_m$(5–10 membered heteroaryl), wherein m is an integer ranging from 0 to 4, and wherein the alkyl, alkenyl, aryl, heteroaryl and alkynyl moieties of the foregoing $R^5$ and $R^6$ groups are optionally substituted by 1 to 3 substituents independently selected from the group consisting of halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and 5–10 membered heteroaryl; or $R^5$ and $R^6$ may be taken together to form a 4–7 membered saturated ring or a 5–10 membered heteroaryl ring, wherein said saturated and heteroaryl rings optionally include 1 or 2 heteroatoms selected from O, S, and N, in addition to the nitrogen to which $R^5$ and $R^6$ are attached, said saturated ring optionally includes 1 or 2 carbon-carbon double or triple bonds, and said saturated and heteroaryl rings are optionally substituted by 1 to 3 substituents independently selected from the group consisting of halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and 5–10 membered heteroaryl;

$R^7$ is H, $C_1$–$C_{10}$ alkyl, $C_2$–$C_{10}$ alkenyl, $C_2$–$C_{10}$ alkynyl, —$(CH_2)_mC_6$–$C_{10}$ aryl, —$(CH_2)_m$(5–10 membered heteroaryl), wherein m is an integer ranging from 0 to 4, and wherein the alkyl, alkenyl, aryl, heteroaryl and alkynyl moieties of the foregoing $R^5$ and $R^6$ groups are optionally substituted by 1 to 3 substituents independently selected from the group consisting of halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and 5–10 membered heteroaryl;

each $R^8$ and $R^9$ is independently H, hydroxy, $C_1$–$C_6$ alkoxy, $C_1$–$C_6$ alkyl, $C_2$–$C_6$ alkenyl, $(CH_2)_m(C_6$–$C_{10})$ aryl, $(CH_2)_m$(5–10 membered heteroaryl), wherein m is an integer ranging from 0 to 4, or $C_2$–$C_{10}$ alkylyl; and Me is methyl which comprises treating a compound of the formula

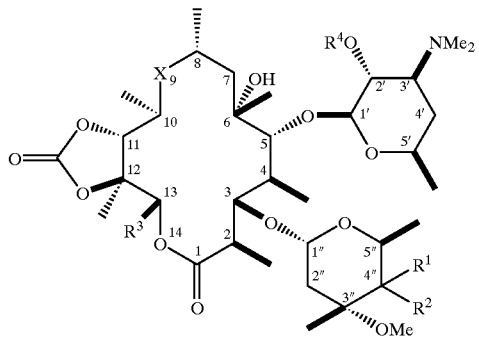

2 wherein X, $R^1$, $R^2$, $R^3$ and $R^4$ are defined as above, with a compound of the formula $HNR^5R^6$, wherein $R^5$ and $R^6$ defined above.

10. The process of claim 9 wherein a compound of formula 2 is prepared by treating a compound of the formula

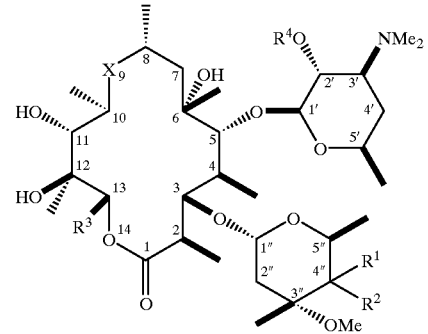

3 wherein X, $R^1$, $R^2$, $R^3$ and $R^4$ are as defined in claim 9 with a $C_1$–$C_4$ alkenyl carborate in the presence of a base.

* * * * *